United States Patent
Naguib

(12)
(10) Patent No.: US 6,780,440 B2
(45) Date of Patent: Aug. 24, 2004

(54) HERBAL COMPOSITIONS AND METHODS FOR DIABETES AND WEIGHT LOSS MANAGEMENT

(76) Inventor: Yousry M. A. Naguib, 602 Fairview Ave., Apt. #31, Arcadia, CA (US) 91007

( * ) Notice: Subject to any disclaimer, the term of this patent is extended or adjusted under 35 U.S.C. 154(b) by 0 days.

(21) Appl. No.: 10/059,370

(22) Filed: Jan. 31, 2002

(65) Prior Publication Data

US 2003/0143291 A1 Jul. 31, 2003

(51) Int. Cl.[7] ............................. A61K 9/20; A61K 9/48; A61K 7/00; A61K 35/78
(52) U.S. Cl. ...................... 424/725; 424/401; 424/451; 424/464
(58) Field of Search ................................. 424/401, 451, 424/464, 725, 439, 480, 452, 465

(56) References Cited

U.S. PATENT DOCUMENTS 6,428,822 B1 * 8/2002 Shi et al. ..................... 424/764
6,451,355 B1 * 9/2002 Reisner ....................... 424/725

FOREIGN PATENT DOCUMENTS

EP 0 561 195 A1 * 9/1993

OTHER PUBLICATIONS

Khleifat et al., "Effect of Ferula homonis extract on social aggression, fertility and some physiological parameters in prepuberta male mice", Endocr J Aug. 2001; 48(4):473–82.*

Artermis Herbs Limited, "Quality, organic herbal tinctures, creams and oil" 2001–2002.*

Prakash et al., "Postcoital contraceptive action in rats of a hexane extract of the aerial parts of Ferula jaeschkeana"; J Ethnopharmacol Sep. 1991; 34(2–3): 221–34.*

El–Thaher et al., "Ferula harmonis 'zallouh' and enhancing erectile function in rats: efficacy and toxicity study"; Int J Impot Res Aug. 2001; 13 (4): 247–51.*

* cited by examiner

*Primary Examiner*—Thurman K. Page
*Assistant Examiner*—S. Tran

(57) ABSTRACT

Herbal compositions and methods suitable for weight loss management and for treating diabetes are disclosed. The compositions comprise *Ferula hermonis* or an extract thereof, or *Ferula hermonis* with selected herbs, extracts thereof, and mixture thereof. The methods of reducing weight, and treating diabetes in patients involve oral administration of the compositions. The invention further relates to a method of extracting and standardizing *Ferula hermonis* extracts and tincture useful for human health.

5 Claims, No Drawings

HERBAL COMPOSITIONS AND METHODS FOR DIABETES AND WEIGHT LOSS MANAGEMENT

DESCRIPTION

FIELD OF THE INVENTION

The invention relates to herbal compositions for weight loss management and treating diabetes in humans. The invention further relates to a method comprising the composition for reducing weight and treating diabetes in humans. The invention further relates to a method for extraction and standardization of a *Ferula hermonis* extract useful for human health.

BACKGROUND OF THE INVENTION

Obesity and overweight are associated with diabetes, hypertension and other diseases that cause morbidity, mortality and high health-care expenditure.

Obesity is the number one nutritional problem in the U.S. An estimated one third of Americans are overweight, with an additional 25 percent being classified as obese. Being overweight significantly increases a person's risk of developing diabetes, heart disease, stroke, and other diseases. Diabetes is a chronic disease that affects 16 million people in the U.S., and more than 125 million people worldwide. Diabetes is the fourth-leading cause of death by disease in the United States. About two-thirds of the nearly 16 million people with type II diabetes in the U.S. are overweight, according to the American Diabetes Association. This form of the disease occurs when the body does not properly respond to insulin. The body uses insulin, a hormone, to help regulate the blood level of glucose, or blood sugar.

In people with diabetes, the pancreas produces little or no insulin, the hormone responsible for facilitating uptake of glucose by cells to give energy as ATP, resulting in a high level of glucose in the blood, causing excessive urination and constant thirst and hunger.

There are two main types of diabetes mellitus, Type I and Type II. In Type I, the more severe form and accounts for 5 to 10 percent diabetes, the body does not produce any insulin, most often occurring in children and young adults. Without regular injections of insulin the sufferer lapses into a coma and dies. Individuals suffering from Type I diabetes are totally insulin dependent.

Type II diabetes, the most prevalent type of diabetes, is usually of gradual onset and occurs mainly in people over 40. Type II diabetes is a metabolic disorder resulting from the body's inability to make enough, or properly use, insulin to meet the body's needs, especially when the person is overweight. It is the most common form of the disease. Type II diabetes accounts for 90 to 95 percent of diabetes. Type II diabetes is nearing epidemic proportions due to a greater prevalence of obesity and sedentary lifestyles. Initially, the combination of dietary measures, weight reduction and oral medication can keep the condition under control for a period of time, but most people with Type II diabetes ultimately require insulin injections.

Medical complications arise from diabetes include athreosclerosis, hyperlipidemia, retinal damage, neurological damage, and blindness.

Diabetes may be controlled with insulin and in some cases through careful diet. There is a need for a safe and effective treatment for diabetes with minimal side effects and without the invasive procedure, such as insulin injection.

Weight loss is considered the cornerstone of treatment in people with Type II diabetes because it allows the body to better use insulin and thus lowers blood sugar. Out-of-control levels of blood sugar are responsible for many of the devastating side effects of diabetes.

Researchers at Harvard found that more than 90 percent of the 3,300 women who developed diabetes over a 16-year study period were overweight, inactive, and smokers. These data come from the ongoing Nurse's Health Study, which began in 1976. The researchers followed 85,000 female nurses who were free of heart disease, diabetes, and cancer at the beginning of the study. The low risk group had a body-mass index (calculated as weight in kilograms divided by the square of height in meters) of less than 25 and a diet high in fibers and polyunsaturated fat and low in trans fat and glycemic load (which reflects the effect of diet on the blood glucose level). Being overweight or obese was the most important diabetes risk predictor, followed by lack of exercise. The study suggests that most of diabetes can be prevented through diet and exercise. Maintaining a healthy weight is the most important way to reduce risk of Type II diabetes. Effective methods for weight reduction are constantly being sought. No one approach, whether dietetic management, or commercial weight loss program, can alone solve the obesity problem. Most weight reduction treatment regimens involve caloric restriction, which is based on the principle that if intake of food is less than energy expenditure, stored calories, will be consumed, mainly in the form of fat. However, once the diet regimen is stopped, weight is quickly regained.

Other treatment regimens are based on the principle of increasing metabolism. By increasing metabolism, calories are burned thereby decreasing body weight. Herbs and their extracts have also been used to control weight, for example U.S. Pat. No. 5,945,107 describes compositions and methods containing herbal plant extracts for weight reduction. Guarana which contains caffeine, as an active ingredient, has been incorporated into weight loss products (Hurel, J. -P., 1993, FR 2 712 191-A1). Primez (Belgium Patent 100593A7) describes a phyto-active mixture referred to as Lycopodium, which contains Guarana and other plant extracts including *Scillia maritime, Ephedra vulgaris*, and *Betula alba* to produce weight loss.

Dietary supplements containing a thermogenic substance, an adrenal support substance, thyrogenic substance and a blood sugar regulation substance are disclosed in U.S. Pat. No. 6,277,396. The thermogenic substance, to increase metabolism and accelerate calorie expenditures, is selected from a group consisting of caffeine, catechins, MaHuang, ephedrine, synephrine, norephedrine, psuedoephedrine, and White Willow. The adrenal support substance, to maintain and/or improve adrenal functions and to reduce stress, is selected from a group consisting of Cordyceps, Ashwagandha, Astragalus, ginseng, Schisandra, Siberian ginseng, licorice, Asian ginseng, Codonopsis, adrenal glandular extract, embryo extract. The thyrogenic substance, to support and/or improve thyroid functions, is selected from a group consisting of Guggul (guggelsterones), thyroid glandular extract, and tyrosine.

The blood sugar regulation substance, to regulate or manipulate blood sugar levels and/or glucose metabolism and to help stabilize normal sugar levels and increase the body's ability to lose stored body fat, is selected from a group consisting of Bitter Melon (*Momordica charantia*), vanadium, allano lactone, Fenugreek (*Trigonella foenumgraecum*), Garcinia (*Garcinia cambogia*), gymnema (*Gymnema sylvestra*), marshmallow (*Althaea officinalis*), chromium, chromium GTF, chromium picolinate, chromium polynicotinate, alpha lipoic acid, inula racemusa, zinc, magnesium, cyclo-hispor, *Agaricus campestris* (mushroom), *Medicago sativa* (Lucema), pinitol (*Bougainvillea spectabilis*).

U.S. Pat. No. 6,042,834 discloses an herbal composition comprising *Trigonella foenum-graecum, Nigella sativa, Origanum vulgare, Rosemarinus officinalis, Lupinus termis, Lawsonia inermis* and *Foeniculum vulgare* for the treatment of diabetes.

Several other herbal compositions have also been developed for reducing weight and treating diabetes in humans; for example U.S. Pat. No. 5,055,460 discloses a composition for reducing weight comprising ephedrine, acetyl salicylic acid and caffeine.

However, none of the compositions and methods for weight reduction or treatment of diabetes in humans disclose a composition and a method consisting *Ferula hermonis* or an extract thereof, or *Ferula hermonis* and one or more of selected herbs or extracts thereof, and mixture thereof, which are disclosed in the present invention.

SUMMARY OF THE INVENTION

The present invention relates to compositions for weight loss management and reducing serum glucose levels in humans by ingesting *Ferula hermonis* or an extract thereof, or *Ferula hermonis* with one or more of selected herbs, or extracts thereof. In one embodiment, *Ferula hermonis* is ingested in an amount of about 2 grams to about 4 grams per day total, preferably in at least 2 doses.

In another aspect, the present invention relates to a method for managing weight loss and hyperglycemia in humans, by ingesting *Ferula hermonis* or extract thereof, or *Ferula hermonis* in combination with one or more of selected herbs. The present invention further relates to a method of extraction and standardization of a *Ferula hermonis* extract useful for human health.

Additional embodiments will be apparent to those skilled in the art with references to the following detailed description.

Ingestion of 3.5 grams of *Ferula hermonis* with meal two times per day for one month resulted in lowering blood sugar, and in weight reduction of 4 to 6 pounds.

DETAILED DESCRIPTION OF THE INVENTION

The present invention relates to a composition comprising the herb *Ferula hermonis* or its extract, or *Ferula hermonis* with one or more of selected herbs that produces weight loss and treats diabetes in patients.

Another object of the present invention is to provide a method of reducing weight and treating diabetes in patients, which comprises administering to the patient a composition of *Ferula hermonis* or its extract, or a combination of *Ferula hermonis* with one or more of selected herbs.

The present invention further comprises at least one herb or an extract thereof capable of promoting weight loss or treating diabetes. The composition of the present invention thus provides a combination of selected herbal extracts, which has been shown to be effective in producing weight loss, and lowering blood sugar in diabetes.

Herbal plant extracts suitable for incorporation into a composition of the present invention for achieving a weight loss include, but is not limited to, herbs disclosed in U.S. Pat. Nos. 5,945,107 and 6,277,396. In addition to ginger, *Citrus aurantium* and Cayenne.

As will be obvious to those of skill in the art, other herbal extracts having these active ingredients can also be selected for use in a composition of the present invention. Herbal extracts for combination into a composition of the present invention are obtained in accordance with methods well known and routine to those of skill in the art.

The herbs of the present invention have been part of folk medicine and have been used for different human ailments and when used as directed no toxicity has been associated with any of them that are reportable.

*Ferula hermonis* (known as Shirsh Zallouh) has recently received much attention due to its commercial value as an aphrodisiac, and as an herbal alternative to Viagra™ without the side effects. Shirsh Zallouh is the Arabic for "hairy root", a perennial of the parsley family.

Shirsh Zallouh has its root in Lebanon; and in northern Lebanon it is called Hashishat al-Kattira, which means herb of abundance. Shirsh Zallouh is a small shrub, with pale pink flowers. It grows at more than 6000 feet on the high mountain areas of northern Lebanon, and on the biblical Mount Hermon in Southern Lebanon, at the joint borders of Syria and Israel.

Shirsh Zallouh roots are usually picked in the summer, after they mature and before the snow-season. There are six different species of the plant Ferula, one of them contained the poison that killed the ancient Greek Philosopher Socrates. *Ferula hermonis* belongs to the family of plants known as the Umbelliferae. This family contains plants like the carrot, fennel, Chinese angelica and hemlock. Hemlock, of course, is extremely poisonous and there are reports that naive ferula hunters are endangering their lives by picking hemlock, which is almost identical in appearance to Ferula.

Zallouh' sexual potency was discovered by goat herders who noticed its strong sexual effects on their herds after eating this plant during the mating season.

Middle East herbalists have used Shirsh Zallouh for centuries as a folk remedy to treat frigidity in women, and erectile and sexual dysfunction in men by increasing blood flow to sexual organs with dazzling results, and have reported renewed vigor, potency and energy. Shirsh Zallouh has been used by the elderly, in the Middle East for centuries to reinvigorate their sex lives.

In humans, the aphrodisiac property and safety of Zallouh has been demonstrated in clinical trials involving more than 7,000 men with erectile dysfunction. The studies found that Zallouh improved sexual function, increased libido and firmness of erections within few days. Zallouh may work immediately for some, and may take few weeks for others.

The efficacy and safety of Zallouh in the treatment of erectile dysfunction was demonstrated in a number of clinical trials. These trials revealed that 60 to 88 percent of men with erectile dysfunction experienced improved erections and increased desire within a few weeks after taking Zallouh root; less than 4 percent experienced side effects such as headaches and flushing. The studies also found that Zallouh may work almost immediately for some, and may take several weeks for others.

Zallouh root also contains naturally occurring vitamins (A, B1, B2, B6, C, D, and E) and minerals (iron, magnesium, selenium, and zinc).

The traditional Lebanese way to take this herb is to slit the root and wait for the resin to ooze out. This process is now replaced by the more efficient extraction procedure. Lebanese pharmacists cut up the root and make an extract by a hot extraction and distillation. It is recommended that men take 50 drops (two and half ml) of an alcohol (alcohol concentration of over ninety percent) extract of Zallouh root at night and again first thing in the morning. This regimen should be followed for at least four weeks. For women suffering from menstrual/menopausal complaints, 50 drops three times daily, after meals. The roots can also be soaked in wine or ground into powder and then taken in capsules or mixed with tea. In Syria, the powder is mixed with honey.

The suggested dose ranges from two to eight grams of Zallouh root taken as a tea. Some studies also indicated that a significant number of males experienced increased number of erections by taking Zallouh one to three hours prior to the anticipated sexual encounter.

Because of the vasodilatation effects of Zallouh, people with cardiovascular or neurological disorder should consult a heath care professional before taking this supplement. The common side effects associated with Zallouh are headaches, flushing, and gastrointestinal tract.

Profiling of Sesquiterpenes from *Ferula Hermonis* Using LC/MS

Liquid chromatography/mass spectroscopy (LC/MS) method was used for the determination and profiling of sesquiterpenes in *Ferula hermonis* extracts.

Ferula genus (Umbelliferae) constitutes about 150 species, and these are widely distributed throughout the Mediterranean area to central Asia. Medicinal properties of Ferula plants include antispasmodic, carminative, digestive, expectorant, sedative, antihysteric, laxative, aphrodisiac, antiseptic, and analgesic. The genus ferula species are rich in the sesquiterpenes daucanes, humulanes, carotanes, himachalanes, and guaianes.

Previous phytochemical investigations on *Ferula hermonis* revealed the presence of α-bisabolol and the daucane sesquiterpenes: 8,9-epoxy jaeschkeanadiol benzoate (epoxy ferutinol benzoate, (3)), jaeschkeanadiol vanillate (ferutinol vanillate, (4)), jaeschkeanadiol p-hydroxybenzoate (ferutinin, (1)), jaeschkeanadiol benzoate (Teferdin, (2)), jaeschkeanadiol (ferutinol, (5)), 8,9-epoxy jaeschjeanadiol (12), 14-(14'-hydroxybenzoyloxy) dauc-4,8-diene(6),and 14-(14'-hydroxy-3'-methoxy-benzoyloxy) dauc-4,8-diene (7).

Compounds (1) and (6) have been shown to exhibit antimicrobial activity against *Staphylococcus aures* and Methicillin-resistant *s. aureus*. Ferutinine (1) and Tenuferidine (11) have been shown to have esterogenic activity, and may contribute to its aphrodisiac activity.

In a recent study on HPLC analysis of *Ferula hermonis*, compounds (1), (2), (3), and (4) were quantified as the marker sesquiterpenes esters, with (1) and (2) as the major components. We used liquid chromatography coupled with mass spectroscopy to standardize *Ferula hermonis* products, and I discovered sesquiterpenes (8), (9), (10) and (11) not previously reported in *Ferula hermonis*.

Development of accurate quantitative profile of analysis for specific marker compounds in herbal manufacturing is critical for determining the quality and consistency of raw materials and finished products. To identify the individual peaks in the HPLC chromatogram of the *Ferula hermonis* extract, we used LC-atmospheric pressure chemical ionization in both the positive and negative mode MS analyses In accordance with previous phytochemistry studies, the mass spectrum of a methanol extract of *Ferula hermonis* we obtained showed peaks in the positive ion mode at m/z=341 and m/z=371 corresponding to compounds (6) and (7), respectively; and peaks in the negative mode at m/z=357 and m/z=341 corresponding to compounds (1) and (2), respectively. In addition to ions at m/z 325 (positive mode); and 373, and 389 (negative mode), which we assigned to compounds ((14-benzoyloxy)dauc-4,8-diene, (10)); (8,9-epoxy jaeschkeanadiol p-hydroxybenzoate, Tenuferidin (11)); and (8,9-epoxy jaeschkeanadiol m,p-dihoxybenzoate, (9)), respectively; and a peak at m/z=373 (positive mode) corresponding to jaeschkeandiol p-methoxybenzoate (8). The Teferdin (4) was also seen in the mass spectrum of the alcoholic tincture at 387 (negative mode), Table (1).

The 14-benzoyloxy-daucane esters (6) and (7) were co-eluted at 9.5 minutes, with (M+1)$^+$ at m/z 341 and 371, respectively; followed by (10) with a retention time (rt) 11.9 minutes and (M+1)$^+$ at m/z 325. All the peaks at m/z 341, 371, 325 (in the positive mode) showed m/z 203 corresponding to M-ester group (122 for benzoate, 168 for vanillate, 138 for p-hydroxy benzoate). The epoxy jaeschkeanadiol derivatives were eluted in the following order: (9) (rt=6.4 min), (11) (rt=6.8 min); and the jaeschkeanadiol derivative (1) at rt=9.4 min.

Compounds (2) and (4) were also observed in the alcoholic tincture of *Ferula hermonis*.

Compounds (8), (9), (10), and (11) were not reported in the previous phytochemistry studies on *Ferula hermonis*.

TABLE 1

Pertinent parameters of the LC/MS analyses of *Ferula hermonis* extracts

| Compound | rt(min) | (M − 1)$^+$ | (M + 1)$^+$ |
|---|---|---|---|
| 2 | 1.52 | 341 | |
| 4 | 1.52 | 387 | |
| 9 | 6.3 | 389 | |
| 8 | 6.4 | 371 | |
| 11 | 6.8 | 373 | |
| 1$^c$ | 9.4 | 357 | |
| 6$^a$ | 9.5 | | 341 |
| 7$^b$ | 9.5 | | 371 |
| 10 | | | 325 |
| 8 | | | 373 |

$^a$14-(4'-hydroxybenzoyloxy)dauc-4,8-diene
$^b$14-(4'-hydroxy-3'-methoxybenzoyloxy)dauc-4,8-diene
$^c$jaeschkeanadiol-p-hydroxybenzoate

TABLE 2

| Compound | Formula | Calculated | Found |
|---|---|---|---|
| 9 | $C_{22}H_{30}O_6$ | 389.1964 | 389.1961 |
| 1 | $C_{22}H_{30}O_4$ | 357.2066 | 357.2075 |
| 6 | $C_{22}H_{28}O_3$ | 341.2116 | 341.2118 |
| 7 | $C_{23}H_{30}O_4$ | 371.2222 | 371.2211 |
| 10 | $C_{22}H_{28}O_2$ | 325.2167 | 325.2177 |
| 2 | $C_{22}H_{30}O_3$ | 373.2379 | 373.2368 |
| 8 | $C_{23}H_{32}O_4$ | 389.1964 | 389.1961 |

Numerous modifications and variations of the present invention are possible in light of the above teachings. It is therefore to be understood that within the scope of the attendant claims attached hereto, this invention may be practiced otherwise than as specifically disclosed herein.

As will be apparent to persons skilled in the art, modifications and adaptations to the above-described invention can be made without departing from the spirit and scope of the invention.

From the foregoing description, it will be apparent to one of ordinary skill in the art that certain modifications and changes can be made without departing from the spirit and scope of the invention.

REFERENCES

Hu F B, Manson J E et al. Diet, Life style, and the risk of Type 2 diabetes mellitus in women. The New England Journal of Medicine 2001; 345:790–797

Al-Yahia M A, Muhammad I, Mirza H H, El-Feraly F S. Antibacterial constituents from the rhizomes of Ferula communis. *Phytotherapy Research* 1998; 12:335–339

Khleifat K, Homady M H, Tarawneh K A, Shakhanbeh J. Effect of ferula hormonis extract on social aggression, fertility and some physiological parameters in prepubertal male mice. *Endocr J* 2001; 48:473

El-Thaher T S, Matalka K Z, Taha H A, Badwan A A. Ferula harmonis 'Zaalouh' and enhancing erectile function in rat-efficacy and toxicity study. *Int J Impot Res* 2001; 13:247

Ahmed AA. Daucanes and other constituents from *Ferula sinaica. Phytochemistry* 1991; 30:1207–1210

Abramov A Y, Zamaraeva M V, Hagelgans A I, Azimov R R, Krasilnikov O V. Influence of plant terpenoids on the permeability of mitochondria and lipid bilayers. *Biochimica et Biophysica Acta* 2001; 1512:98

Galal A. Sesquiterpenes from *Ferula hermonis* Boiss. *Pharmazie* 2000; 55:961–962

Galal A M, Abourashed E A, Ross S A, ElSohly M A, Al-Said, M S, El-Feraly F S. Daucane sesquiterpenes from *Ferula hermonis. J Nat Prod* 2001; 64:399–400

Abourashed E A, Galal A M, El-Feraly, Khan I A. Separation and quantification of the major Daucane esters of *Ferula hermonis* by HPLC. *Planta Med* 2001; 67:681

What is claimed is:

1. An oral herbal composition for the treatment of diabetes and weight loss management in patients consisting of 0.01 to 4.0 grams of *Ferula hermonis*, wherein *Ferula hermonis* consists of the sesquiterpenes: 8,9-epoxy jaeschkeanadiol benzoate (epoxy ferutinol benzoate, (3)): jaeschkeandiol vanillate (ferutinol vanillate, (4)); jaeschkeanadiol p-hydroxybenzoate (ferutinin, (1)); jaeschkeanadiol benzoate (Teferdin, (2)); jaeschkeanadiol (ferutinol, (5)) 8,9-epoxy jaeschjeanadiol (12); 14-(14'-hydroxybenzoyloxy) dauc-4,8-diene (6); 14-(14'-hydroxy-3'-methoxybenzoyloxy) dauc-4,8-diene (7); 14-benzoyloxy-dauc-4,8-diene (10); 8,9-epoxy jaeschkeanadiol p-hydroxybenzoate (Tenuferidin (11)); and jaeschkeanadiol p-methoxybenzoate (8); 8,9-epoxy jaeschkeanadiol m,p-dihydroxybenzoate (9), with one or more of selected herbs, and mixture thereof.

2. The composition according to claim 1, wherein the selected herb in an effective amount is selected from the group consisting of, but not limited to, Gaurana, Garcinia cambogia, Ginkgo, Ginseng, Senna, Juniper, Citrus aurantium, Cichorium, Ephedra, White Willow bark, Oolong tea, Chromium, Carnitine, Green tea extract, Ginger, Licorice, Cayenne, Gymnema sylvestre, Bitter melon, Neem, Nigella sativa, Foeniculum vulgare (Fennel), Salvia officinalis (Sage), Rosemarinus officinalis (Rosemary), Fenugreek, Majoram, Lupinus termis (Egyptian lupin), Airelle, Eucalyptus, Rheum Rhubarb, Thyme, Alpha lipoic acid, Alpinia officinarum, Colchicum, Hawthorn, Cupressus sempervirens, Phaselous vulgaris, Tamarindus indica, Aloe.

3. The composition of claim 1, wherein *Ferula hermonis* extract is extracted by a process consists of:

(a) extracting *Ferula hermonis* roots with a suitable solvent, including water, an alkyl alcohol, or a nonpolar organic solvent with heating for 5 hours and stirring, and then further stirred at room temperature for 24 hours, (b) filtering the resulting extract through a cloth or a filter papa to yield a tincture or a filtrate, (c) concentrating the filtrate to a small volume, which on standing at room temperature yield a *Ferula hermonis* extract, or (d) evaporating the solvent under vacuum at 40° C. to yield *Ferula hermonis* extract.

4. A method of reducing weight end treating diabetes in patients consists of administration of the composition of claim 1.

5. The method of claim 4, wherein *Ferula hermonis* is made by the process of claim 3.

* * * * *